(12) United States Patent
Izawa et al.

(10) Patent No.: US 9,598,388 B2
(45) Date of Patent: *Mar. 21, 2017

(54) METHOD FOR PRODUCING TETRAHYDROFURAN

(71) Applicant: MITSUBISHI CHEMICAL CORPORATION, Chiyoda-ku (JP)

(72) Inventors: Yusuke Izawa, Mie (JP); Masaru Utsunomiya, Tokyo (JP); Norikazu Konishi, Mie (JP); Kouta Tanaka, Mie (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/147,932

(22) Filed: Jan. 6, 2014

(65) Prior Publication Data

US 2014/0179935 A1   Jun. 26, 2014

Related U.S. Application Data

(63) Continuation of application No. PCT/JP2012/067012, filed on Jul. 3, 2012.

(30) Foreign Application Priority Data

| Jul. 4, 2011 | (JP) | ................................. | 2011-148327 |
| Jul. 4, 2011 | (JP) | ................................. | 2011-148328 |
| Jul. 8, 2011 | (JP) | ................................. | 2011-151716 |
| Jul. 13, 2011 | (JP) | ................................. | 2011-154862 |
| Aug. 1, 2011 | (JP) | ................................. | 2011-168645 |
| Nov. 1, 2011 | (JP) | ................................. | 2011-240422 |
| Nov. 2, 2011 | (JP) | ................................. | 2011-241572 |

(51) Int. Cl.
  *C07D 307/02* (2006.01)
  *C07D 307/08* (2006.01)

(52) U.S. Cl.
  CPC .................. *C07D 307/08* (2013.01)

(58) Field of Classification Search
  CPC ............................ C07D 307/08; C08G 65/20
  USPC .................................. 549/509; 502/217, 349
  See application file for complete search history.

(56) References Cited

U.S. PATENT DOCUMENTS

| 3,467,679 A | 9/1969 | Rogers |
| 4,511,708 A | 4/1985 | Kasuga et al. |
| 6,137,016 A | 10/2000 | Wood et al. |
| 6,387,224 B1* | 5/2002 | Pinkos |
| 7,098,349 B2* | 8/2006 | Pinkos ................. C07D 307/08 549/509 |
| 7,985,566 B2 | 7/2011 | Aoshima et al. |
| 2006/0122365 A1* | 6/2006 | Pinkos |
| 2007/0260073 A1 | 11/2007 | Wood et al. |

FOREIGN PATENT DOCUMENTS

| CN | 1675190 A | 9/2005 |
| JP | 48-1075 | 1/1973 |
| JP | 48-1075 B | 1/1973 |
| JP | 50-137907 A | 11/1975 |
| JP | 57-147515 A | 9/1982 |
| JP | 59-140223 A | 8/1984 |
| JP | 61-126080 A | 6/1986 |
| JP | 61-197534 A | 9/1986 |
| JP | 62-199617 A | 9/1987 |
| JP | 62-225523 A | 10/1987 |
| JP | 02-167274 | 6/1990 |
| JP | 7-10981 A | 1/1995 |
| JP | 07-118253 | 5/1995 |
| JP | 7-118253 A | 5/1995 |
| JP | 2001-114884 A | 4/2001 |
| JP | 2003-26622 A | 1/2003 |
| JP | 2006-503050 | 1/2006 |
| JP | 2006-503050 T | 1/2006 |
| JP | 2008-101143 A | 5/2008 |
| JP | 2008-514684 T | 5/2008 |
| JP | 4582228 B2 | 9/2010 |
| JP | 2013-04966 A | 3/2013 |
| JP | 5939061 B2 | 5/2016 |
| JP | 5949227 B2 | 6/2016 |
| WO | 2004/026853 | 4/2004 |

OTHER PUBLICATIONS

International Search Report issued Aug. 14, 2012 in PCT/JP2012/067012 filed Jul. 3, 2012.
U.S. Appl. No. 14/147,894, filed Jan. 6, 2014, Izawa et al.
U.S. Appl. No. 14/147,932, filed Jan. 6, 2014, Izawa et al.
Extended European Search Report issued on Jun. 18, 2014 in the corresponding European Application No. 12807799.7.
Combined Chinese Office Action and Search Report issued Sep. 24, 2014 in Patent Application No. 201280032871.0 (with English Translation and English Translation of Category of Cited Documents).
European Office Action dated May 5, 2015, in European Patent Application No. 12807799.7.
European Office Action dated Nov. 24, 2015, in European Patent Application No. 12807799.7 (4 pages).
Japanese Office Action dated Dec. 8, 2015, in Japanese Patent Application No. 2012-149938 with English Translation (6 pages).
Japanese Office Action mailed Jan. 26, 2016 (Date of Drafting: Jan. 19, 2016), in Japanese Patent Application No. 2012-149937 with English Translation (9 pages).

(Continued)

*Primary Examiner* — T. Victor Oh
(74) *Attorney, Agent, or Firm* — Oblon, McClelland, Maier & Neustadt, L.L.P.

(57) ABSTRACT

The present invention is concerned with a method for producing tetrahydrofuran including carrying out a dehydration cyclization reaction of 1,4-butanediol in the presence of an acid catalyst having a pKa value of not more than 4 within a reactor, wherein a raw material liquid containing 1,4-butanediol to be provided for the reaction contains from 0.01 to 0.35% by weight of 2-(4-hydroxybutoxy)-tetrahydrofuran and 1 ppm by weight or more and not more than 1,000 ppm by weight of at least one of an amine and an amide in terms of a concentration as converted into a nitrogen atom.

19 Claims, No Drawings

(56) References Cited

OTHER PUBLICATIONS

Japanese Office Action mailed Jan. 26, 2016 (Date of Drafting: Jan. 19, 2016), in Japanese Patent Application No. 2012-152803 with English Translation (8 pages).
Japanese Office Action mailed Feb. 23, 2016 (Date of Drafting: Feb. 17, 2016), in Japanese Patent Application No. 2012-149684 with English Translation (6 pages).
Japanese Office Action issued Jul. 19, 2016 in Patent Application No. 2012-49938 (with unedited computer generated English translation).
European Office Action issued Sep. 20, 2016 in Patent Application No. 12 807 799.7.
Japanese Office Action mailed Dec. 20, 2016, in Japanese Patent Application No. 2016-064281 (with English Translation)

* cited by examiner

METHOD FOR PRODUCING TETRAHYDROFURAN

TECHNICAL FIELD

The present invention relates to a method for producing tetrahydrofuran, and in particular, a method for producing tetrahydrofuran stably and efficiently by a dehydration cyclization reaction of 1,4-butanediol by using an acid catalyst.

BACKGROUND ART

Tetrahydrofuran (hereinafter sometimes abbreviated as "THF") is a useful compound as a solvent for various organic compounds including polymer compounds, a raw material for polytetramethylene glycol, and the like.

Tetrahydrofuran is frequently produced industrially by a dehydration cyclization reaction of 1,4-butanediol (hereinafter sometimes abbreviated as "1,4BG"). It is known that an acid catalyst is effective as a catalyst for this reaction in any of a homogeneous system or a heterogeneous system.

For example, there is known a method of using a solid catalyst such as a silica alumina catalyst (Patent Document 1), a cation exchange resin (Patent Document 2), etc. This method encounters such a problem that the catalyst deterioration under a high-temperature condition is serious, or the like. In recent years, there is also proposed a method for producing tetrahydrofuran by using a heteropolyacid which is considered to be small in the catalyst deterioration even under a high-temperature condition (Patent Document 3).

When THF is produced by a dehydration cyclization reaction of 1,4BG by using such a catalyst, a liquid phase reactor using a fixed bed reactor, a reactive distillation mode in which a product is distilled off from a reactor through a gas phase part, and the like are used.

Though such a process is operated in a state where a high-boiling component formed as a by-product during the reaction is accumulated in a liquid phase part of the reactor, the formation of a by-product solid is advanced at the same time.

Specifically, Patent Document 3 describes that deposition of a by-product solid such as a polymer, etc. makes the operation difficult and describes the formation of a solid derived from 2-(4-hydroxybutoxy)-tetrahydrofuran (hereinafter sometimes abbreviated as "BGTF") that is a reaction by-product at the time of synthesis of 1,4BG and which is contained as an impurity in a raw material 1,4BG. In order to avoid such deposition of a by-product solid at the time of production of THF, Patent Document 3 describes that a pretreatment method of the catalyst is specified, the content of nitrogen is kept low, or the like.

BACKGROUND ART DOCUMENT

Patent Document

Patent Document 1: JP-B-48-1075
Patent Document 2: JP-A-7-118253
Patent Document 3: JP-T-2006-503050

SUMMARY OF INVENTION

Problem that Invention is to Solve

However, on the occasion of continuously producing THF from the raw material 1,4BG, even if a material in which the concentration of a compound which may possibly cause the formation of a by-product solid in the raw material 1,4BG, for example, BGTF, is reduced to some extent is used, in the process to be operated by accumulating a reaction liquid within a reactor, there was involved such a problem that a by-product in a solid shape is deposited, thereby hindering the continuous production of THF and lowering the productivity.

In view of the foregoing problems, the present invention has been made, and an object thereof is to provide a method for producing tetrahydrofuran industrially advantageously by a dehydration cyclization reaction using 1,4-butanediol as a raw material in the presence of an acid catalyst, wherein deposition of a by-product solid is prevented from occurring, thereby stably obtaining high productivity.

Means for Solving Problem

In order to solve the foregoing problems, the present inventors made extensive and intensive investigations. As a result, it has been found that by making a specified amount of at least one of an amine and an amide present in 1,4BG to be provided for the production of tetrahydrofuran, the amount of 2-(4-hydroxybutoxy)-tetrahydrofuran is reduced within a reactor in the presence of by-product water, whereby the formation of a by-product solid can be effectively inhibited; and that according to this, even when the raw material 1,4-butanediol containing 2-(4-hydroxybutoxy)-tetrahydrofuran which causes the formation of a by-product solid to some extent is used, deposition of a by-product solid within a reactor is prevented from occurring, thereby enabling one to stably keep high productivity.

The present invention has been achieved on the basis of such knowledge, and its gist includes the following [1] to [7].

[1] A method for producing tetrahydrofuran, comprising:
carrying out a dehydration cyclization reaction of 1,4-butanediol in a presence of an acid catalyst having a pKa value of not more than 4 within a reactor,
wherein a raw material liquid containing 1,4-butanediol to be provided for the reaction contains from 0.01 to 0.35% by weight of 2-(4-hydroxybutoxy)-tetrahydrofuran and 1 ppm by weight or more and not more than 1,000 ppm by weight of at least one of an amine and an amide in terms of a concentration as converted into a nitrogen atom.

[2] A method for producing tetrahydrofuran, comprising:
carrying out a dehydration cyclization reaction of 1,4-butanediol in a presence of an acid catalyst having a pKa value of not more than 4 within a reactor,
wherein a reaction liquid within the reactor contains 1 ppm by weight or more and not more than 10,000 ppm by weight of at least one of an amine and an amide in terms of a concentration as converted into a nitrogen atom.

[3] The method for producing tetrahydrofuran as described in [1],
wherein a reaction liquid within the reactor contains 1 ppm by weight or more and not more than 10,000 ppm by weight of at least one of an amine and an amide in terms of a concentration as converted into a nitrogen atom.

[4] The method for producing tetrahydrofuran as described in any one of [1] to [3],
wherein a reaction liquid within the reactor contains 0.1% by weight or more and not more than 10% by weight of water.

[5] The method for producing tetrahydrofuran as described in any one of [1] to [4], comprising:

a step of extracting a gas containing tetrahydrofuran and water present in a gas phase part within the reactor into an outside of the reactor.

[6] The method for producing tetrahydrofuran as described in any one of [1] to [5], wherein a temperature of a reaction liquid within the reactor is in a range of 80° C. or higher and not higher than 250° C.

[7] The method for producing tetrahydrofuran as described in any one of [1] to [6], comprising:

a step of heating crude 1,4-butanediol at 80° C. or higher in a presence of at least one of an amine and an amide to reduce a content of 2-(4-hydroxybutoxy)-tetrahydrofuran, followed by feeding into the reactor.

Effects of Invention

According to the present invention, in a method for producing tetrahydrofuran by a dehydration cyclization reaction using 1,4-butanediol as a raw material in the presence of an acid catalyst, the amount of 2-(4-hydroxybutoxy)-tetrahydrofuran can be reduced within a reactor, and therefore, deposition of a by-product solid is prevented from occurring, thereby enabling one to produce tetrahydrofuran in high productivity through a stable operation.

In the present invention, in view of the fact that the amount of 2-(4-hydroxybutoxy)-tetrahydrofuran can be reduced during a dehydration cyclization reaction, even when a raw material 1,4-butanediol containing 2-(4-hydroxybutoxy)-tetrahydrofuran which causes the formation of a by-product solid to some extent is used, a problem of the deposition of a by-product solid can be avoided, and therefore, costs and time required for purification of the raw material 1,4-butanediol can be reduced.

In addition, the deposition of a by-product solid can be prevented from occurring in a reaction step, and therefore, in the case of providing a purification step as a post-step of the reaction step, even an effect for preventing the occurrence of staining such as fixation of a solid, etc. in purification facilities (for example, a column bottom of distillation column, etc.) in the purification step can be obtained, so that it is possible to contemplate to achieve stable operation of the entire production facilities of tetrahydrofuran.

MODE FOR CARRYING OUT INVENTION

The method for producing tetrahydrofuran according to the present invention is concerned with a method for producing tetrahydrofuran comprising carrying out a dehydration cyclization reaction of 1,4-butanediol in the presence of an acid catalyst having a pKa value of not more than 4 within a reactor, wherein the content of 2-(4-hydroxybutoxy)-tetrahydrofuran in a raw material liquid containing 1,4-butanediol within the reactor at the time of start of the dehydration cyclization reaction is from 0.01 to 0.35% by weight, and the content of at least one of an amine and an amide is 1 ppm by weight or more and not more than 1,000 ppm by weight in terms of a concentration as converted into a nitrogen atom, or at least one of an amine and an amide in a reaction liquid within the reactor is present in a concentration, as converted into a nitrogen atom, of 1 ppm weight or more and not more than 10,000 ppm by weight.

1,4-Butanediol 1,4BG which is used in the present invention can be obtained by a known method.

For example, 1,4BG can be produced by hydrogenating 1,4-diacetoxy-2-butene obtained by diacetoxylation of butadiene, followed by hydrolysis. Alternatively, 1,4BG obtained by hydrogenation of maleic anhydride, 1,4BG derived from acetylene by the Reppe method, 1,4BG obtained through oxidation of propylene, 1,4BG obtained by a fermentation method, or the like can also be used.

In general, 1,4BG produced by such a method contains BGTF that is a reaction by-product, 1-acetoxy-4-hydroxybutane, a dehydrated dimer or dehydrated trimer of 1,4-butanediol, γ-butyrolactone, or the like as an impurity. In particular, the content of BGTF is generally from 0.01 to 0.5% by weight.

In the present invention, the raw material 1,4BG which is fed into the reactor for producing THF by means of a dehydration cyclization reaction is not particularly limited so far as the BGTF concentration in the raw material liquid falls within a range as described later. However, the content of BGTF in the raw material liquid containing 1,4BG to be fed into the reactor is from 0.01 to 0.35% by weight, preferably from 0.10% by weight to 0.33% by weight, and more preferably from 0.15% by weight to 0.30% by weight.

For that reason, in the present invention, it is preferable to feed the raw material 1,4BG into the reactor after carrying out a treatment for reducing the BGTF concentration in crude 1,4BG produced by the above-described known method, as the need arises.

This treatment for reducing the BGTF concentration in the crude 1,4BG is not particularly limited, and though a usual separation operation such as distillation, etc. can be adopted, a method of heating the crude 1,4BG at 80° C. or higher in the presence of an amine and water is preferable. That is, when the crude 1,4BG is heated in the presence of an amine and water, BGTF is converted into 2-hydroxytetrahydrofuran, or 4-hydroxybutyl aldehyde that is a ring-opened product thereof or its derivative. Among them, 2-hydroxytetrahydrofuran does not hinder the dehydration cyclization reaction and does not cause the formation of a by-product solid, and moreover, after the dehydration cyclization reaction, it can be easily separated from 1,4BG or THF by means of distillation or the like. In addition, it is possible to convert 2-hydroxytetrahydrofuran into 1,4-butanediol by means of hydrogenation.

In this heat treatment, a method of making at least one of an amine and an amide present in the crude 1,4BG is not particularly limited. However, a method of mixing the crude 1,4BG with one or two or more members selected from an amine-based compound represented by the following formula (1) and a decomposition product thereof and an amide represented by the following formula (2) and a decomposition product thereof; a method of bringing the crude 1,4BG into contact with an anion exchange resin having a polyamine skeleton, thereby eluting an amine component contained in the anion exchange resin into the crude 1,4BG; and the like are preferable.

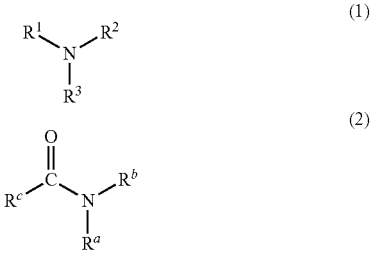

Incidentally, in the formula (1), each of $R^1$ to $R^3$ independently represents a hydrogen atom, an alkyl group, an alkenyl group, an aryl group, an alkoxy group, a hydroxyl group, an amino group, an alkylthio group, or an arylthio group; each of these groups may further have a substituent; and a hetero atom may be contained in the substituent. In addition, $R^1$ to $R^3$ may be the same as or different from each other.

In addition, a primary amide, a secondary amide, and a tertiary amide can be used as the carboxylic acid amide represented by the formula (2). An N-alkyl-substituted amide, an N-alkenyl-substituted amide, an N-aryl-substituted amide, and the like, namely a carboxylic acid amide in which one or both of the substituents $R^a$ and $R^b$ are any one of an alkyl group, an alkenyl group, and an aryl group, and the like, are used in the N-substituted substituent number in the range of from 0 to 2. In addition, a hetero atom may be contained in the substituents $R^a$ and $R^b$, and the substituents $R^a$ and $R^b$ may be the same as or different from each other. On the other hand, examples of the substituent $R^c$ on the carbonyl side include a hydrogen atom, an alkyl group, an alkenyl group, an aryl group, and the like.

In addition, the above-described substituents $R^a$ to $R^c$ may be connected to each other to form a ring. An alkyl group is preferable as the substituent $R^c$ on the carbonyl side from the viewpoint that side reaction, decomposition, or the like can be inhibited.

When the amount of the amine and the amide in the crude 1,4BG to be provided for the heat treatment is excessively small, the effect for reducing the BGTF concentration cannot be sufficiently obtained, whereas what it is excessively large becomes a factor in the hindrance of the subsequent dehydration cyclization reaction, and therefore, the amount of the amine and the amide in the crude 1,4BG is preferably from 1 to 10,000 ppm by weight, and especially preferably from 1 to 1,000 ppm by weight in terms of a concentration as converted into a nitrogen atom (hereinafter sometimes abbreviated as "nitrogen concentration").

In addition, when the heating temperature at the time of heat treatment is too low, the effect for reducing the BGTF concentration cannot be sufficiently obtained, whereas when it is too high, the impurities are increased due to an increase of the heating cost and an increase of the side reaction. Therefore, this heating temperature is usually 80° C. or higher, preferably from 100 to 250° C., and more preferably from 120 to 200° C. The heating time varies with the heating temperature and is arbitrarily set up. The heating time is usually one minute or more and not more than 100 hours, and preferably 5 minutes or more and not more than 10 hours.

Though a method for this heat treatment is not particularly limited, heating can be carried out by a distillation column, an extraction vessel, a conduit, a heat exchanger, or the like.

Incidentally, the crude 1,4BG to be provided for this heat treatment is preferably one having a content of BGTF of from 0.04 to 0.5% by weight and a water concentration of from 1.0 to 25% by weight.

When the content of BGTF in the crude 1,4BG to be provided for the heat treatment is excessively high, a load in the treatment for reducing the BGTF concentration increases, so that the treatment cost becomes high. In the case where the content of BGTF is sufficiently low, the treatment for reducing the BGTF concentration by this heat treatment becomes unnecessary. The content of BGTF in the crude 1,4BG to be provided for the heat treatment is more preferably from 0.05 to 0.45% by weight, and still more preferably from 0.06 to 0.4% by weight.

In addition, when the water concentration of the crude 1,4BG to be provided for the heat treatment is too high, the heating cost becomes excessive, whereas it is too low, the effect for converting BGTF in the presence of an amine to reduce the BGTF concentration cannot be sufficiently obtained. The water concentration of the crude 1,4BG to be provided for the heat treatment is more preferably from 2 to 20% by weight, and still more preferably from 5 to 16% by weight.

In consequence, in the case where the content of BGTF or the water concentration of the crude 1,4BG to be provided for the heat treatment falls outside the foregoing preferred range, it is preferable to carry out component adjustment such as hydrogenation, distillation, etc.

In addition, the crude 1,4BG to be provided for the heat treatment preferably has a pH of 7 or more. That is, by heating the crude 1,4BG containing a prescribed amount of an amine and having a pH of 7 or more in a state where it contains water, it is possible to reduce the BGTF more efficiently.

In crude 1,4BG having a pH of less than 7, THF is formed by the heat treatment before being introduced into a reactor, thereby, for example, causing an increase of differential pressure of a distillation column or a loss of 1,4BG. On the other hand, so far as the crude 1,4BG having a pH of 7 or more is concerned, the formation of THF at the time of heat treatment can be inhibited. As for the crude 1,4BG having a pH of 7 or more, in the case where the pH of crude 1,4BG produced by the above-described known technology is 7 or more, such crude 1,4BG can be used as it is. In addition, even in the case where the pH of this crude 1,4BG is less than 7, the pH can be increased to 7 or more by means of addition of the above-described amine, contact with an anion exchange resin having an amine skeleton, or the like.

The pH of the crude 1,4BG to be provided for the heat treatment may be 7 or more. What the pH is excessively high becomes a factor in the catalyst deterioration at the time of production of THF, and therefore, the pH is preferably not more than 12, for example, from 7.0 to 12.0.

In the present invention, it is preferable to obtain, as a raw material liquid as described later, a 1,4BG-containing liquid containing from 0.01 to 0.35% by weight of BGTF and from 1 to 1,000 ppm by weight of at least one of an amine and an amide in terms of a nitrogen concentration by such a treatment for reducing the BGTF concentration by means of heating.

Incidentally, after the above-described heat treatment, 1,4BG may be concentrated by means of distillation purification or the like.

[Acid Catalyst]

The acid catalyst which is used in the present invention may be one having a value of pKa (acid dissociation constant) of not more than 4 and capable of subjecting 1,4BG to a dehydration cyclization reaction into THF, and an arbitrary acid catalyst can be used. However, the acid catalyst is preferably sulfonic acid, a cation exchange resin, a heteropolyacid, phosphoric acid, or the like, more preferably a metal-free organic acid or phosphoric acid, and especially preferably an organic sulfonic acid. Specifically, examples thereof include an aromatic sulfonic acid derivative such as p-toluenesulfonic acid, benzenesulfonic acid, o-toluenesulfonic acid, m-toluenesulfonic acid, etc.; a chain aliphatic sulfonic acid derivative such as butanesulfonic acid, hexanesulfonic acid, octanesulfonic acid, nonanesulfonic acid, etc.; and the like. These may have a substituent other than sulfonic acid in a carbon skeleton. These acid catalysts may be used solely or in admixture of two or more kinds thereof. p-Toluenesulfonic acid is especially preferably used as the acid catalyst.

Incidentally, among acid catalysts, an organic sulfonic acid or the like is in general soluble in 1,4BG.

The use amount of the acid catalyst is usually from 0.01 to 20% by weight, preferably from 0.05 to 10% by weight, and especially preferably from 0.2 to 5% by weight in terms of a concentration in the reaction liquid within a reactor.

Incidentally, though it is possible to add the acid catalyst all at once at the time of start of the reaction or before the start, for the purpose of compensating the catalyst deterioration with time, the successive loading is preferable because it is effective for continuing the reaction more stably. In that case, as for the amount of loading with time of the raw material liquid containing 1,4BG into a reactor, the addition amount of the acid catalyst is in the range of preferably from 0.0001 to 0.1% by weight, and especially preferably from 0.0005 to 0.005% by weight in terms of a concentration of the acid catalyst relative to the amount of loading with time of 1,4BG contained in the raw material liquid. In consequence, for example, the raw material liquid to which the acid catalyst has been added so as to fall within the foregoing concentration range may be introduced into a reactor.

[Raw Material Liquid]

The present invention is characterized in that the content of BGTF of the 1,4BG-containing raw material liquid to be provided for the reaction is from 0.01 to 0.35% by weight; and that at least one of the amine and the amide is contained in a nitrogen concentration of from 1 to 1,000 ppm by weight. Incidentally, in the present invention, the raw material liquid refers to a component other than the acid catalyst among the components to be provided in a reactor for the dehydration cyclization reaction.

When the content of BGTF in this raw material liquid is more than 0.35% by weight, the formation amount of a by-product solid tends to increase during the dehydration cyclization reaction, so that the stable production of THF is hindered. On the other hand, when the content of BGTF in the raw material liquid is smaller, the formation amount of a by-product solid can be reduced; however, in order to make the content of BGTF excessively small, a load for purifying the crude 1,4BG becomes excessive, so that such does not suit the object of the present invention to make it possible to avoid a problem regarding the deposition of a by-product solid during the dehydration cyclization reaction even when the raw material 1,4BG from which BGTF has been excessively removed is not used. The content of BGTF in the raw material liquid is preferably from 0.01 to 0.33% by weight, more preferably from 0.02 to 0.30% by weight, and especially preferably from 0.03 to 0.16% by weight.

In addition, when the amount of at least one of the amine and the amide in the raw material liquid is too small, the effect of the present invention for preventing the occurrence of formation of a by-product solid by reducing BGTF derived from 1,4BG during the dehydration cyclization reaction cannot be sufficiently obtained. When the amount of at least one of the amine and the amide is larger, the above-described effect becomes larger; however, when the amount of at least one of the amine and the amide is large, not only the addition cost of at least one of the amine and the amide increases, but at least one of the amine and the amide causes a lowering of the productivity of THF.

In consequence, the amount of at least one of the amine and the amide in the raw material liquid is from 1 to 1,000 ppm by weight, preferably from 2 to 200 ppm by weight, and more preferably from 20 to 80 ppm by weight in terms of a nitrogen concentration.

Incidentally, in the case where the raw material liquid according to the present invention contains only an amine but does not contain an amide, the amount of the amine in the raw material liquid is from 1 to 1,000 ppm by weight, preferably from 2 to 200 ppm by weight, and more preferably from 20 to 80 ppm by weight in terms of a nitrogen concentration. In addition, in the case where the raw material liquid according to the present invention contains only an amide but does not contain an amine, the amount of the amide in the raw material liquid is from 1 to 1,000 ppm by weight, preferably from 2 to 200 ppm by weight, and more preferably from 5 to 60 ppm by weight in terms of a nitrogen concentration.

In addition, in the case where the raw material liquid contains all of an amine and an amide, a total amount of the amine and the amide in the raw material liquid is from 1 to 1,000 ppm by weight, preferably from 2 to 200 ppm by weight, and more preferably from 20 to 80 ppm by weight in terms of a nitrogen concentration.

As for the concentration range of at least one of the amine and the amide, when the lower limit increases, the effect of the present invention tends to be more likely revealed, and when the upper limit decreases, the treatment of post-steps tends to be reduced.

As a method of making at least one of the amine and the amide present in this raw material liquid, a method of adding at least one of the amine and the amide in the raw material liquid; a method of brining the raw material liquid into contact with an anion exchange resin having an amine skeleton, thereby eluting an amine component contained in the anion exchange resin into the raw material liquid; and the like are preferable. An elution fraction from this anion ion exchange resin is a polyamine. The polyamine is a general term of linear aliphatic hydrocarbons in which two or more primary amino groups are bonded to each other, and in the present invention, the polyamine is a polymer containing two or more, and preferably from 3 to 20 constituent units derived from a compound in which any one or more of $R^1$ to $R^3$ of the nitrogen-containing compound represented by the formula (1) represent an alkyl group.

The raw material liquid after adding at least one of the amine and the amide or after contacting the anion exchange resin having an amine skeleton, or the like may be subjected to a separation operation such as distillation, etc.

Examples of the amine which is used herein include a primary amine such as octylamine, nonylamine, 1-aminodecane, aniline, phenethylamine, etc.; a secondary amine such as dipentylamine, dihexylamine, diheptylamine, dicyclohexylamine, N-methylaniline, etc.; a tertiary amine such as tributylamine, tripentylamine, N,N-dimethylaniline, etc.; a diamine such as 1,3-propanediamine, N,N-dimethyl-1,6-hexanediamine, etc.; a 5-membered cyclic amine such as N-butylpyrrole, N-butyl-2,3-dihydropyrrole, N-butylpyrrolidine, 2,3-dihydro-1H-indole, etc.; a 6-membered cyclic amine such as 4-aminomethylpiperidine, 4-dimethylaminopyridine, 1,2,3,4-tetrahydroquinoline, 4-amino-5,6-dihydro-2-methylpyrimidine, 2,3,5,6-tetramethylpyrazine, 3,6-dimethylpyridazine, etc.; and the like. Furthermore, examples of an amine containing an oxygen atom include a chain amino alcohol such as 4-aminobutanol, 2-aminobutanol, etc.; and a cyclic amine such as 2-ethylmorpholine, N-methoxycarbonylmorpholine, prolinol, 3-hydroxypiperidine, 4-hydroxypiperidine, tetrahydrofurfurylamine, 3-aminotetrahydropyran, etc., from the viewpoint that a boiling point thereof is close to that of 1,4BG. Among these amines, a primary or secondary amine having at least one N—H bond or an elution fraction from an anion exchange resin containing a primary polyamine having an N—H bond is preferable. From the standpoint of promoting the decomposition of BGTF, examples of the preferred amine include a primary amine such as octylamine, nonylamine, 1-aminodecane, aniline, phenethylamine, etc.; a secondary amine such as dipentylamine, dihexylamine, diheptylamine, dicyclohexylamine, N-methylaniline, etc.; a diamine such as 1,3-propanediamine, N,N-dimethyl-1,6-hexanediamine, etc.; a 5-membered cyclic amine such as 2,3-dihydro-1H-indole, etc.; a 6-membered cyclic amine such as 4-aminomethylpiperidine, 1,2,3,4-tetrahydroquinoline, etc.; a polymer containing from 2 to 20 constituent units derived from ethyleneamine as eluted from an anion exchange resin having a polyethylenediamine skeleton; and the like. Furthermore, examples of an amine containing an oxygen atom include a chain amino alcohol such as 4-aminobutanol, 2-aminobutanol, etc.; and a cyclic amine such as 2-ethylmorpholine, prolinol, 3-hydroxypiperidine, 4-hydroxypiperidine, tetrahydrofurfurylamine, 3-aminotetrahydropyran, etc., from the viewpoint that a boiling point thereof under atmospheric pressure is close to that of 1,4BG. Furthermore, from the standpoint that a compound having a boiling temperature under atmospheric pressure of from 160 to 260° C. is preferably used, preferred examples thereof include 1-aminodecane, dihexylamine, prolinol, 3-hydroxypiperidine, 4-hydroxypiperidine, 4-aminobutanol, tetrahydrofurfurylamine, and the like.

In addition, preferred examples of the amide which is used in the present invention include an amide having a chain skeleton, such as acetamide, N-methylacetamide, N-ethylacetamide, N,N-dimethylacetamide, etc.; an aromatic amide such as benzamide, etc.; and a cyclic amide such as 2-pyrrolidone, N-methylpyrrolidone, N-ethylpyrrolidone, N-vinylpyrrolidone, 2-piperidone, N-methylpiperidone, etc., from the standpoint that a boiling point under atmospheric pressure thereof is not excessively low as compared with that of 1,4BG and also from the standpoint of stability of a compound. More preferred examples thereof include acetamide, N-methylacetamide, 2-pyrrolidone, and N-methylpyrrolidone, from the standpoint that a boiling point thereof is close to that of 1,4BG that is the raw material. 2-Pyrrolidone or N-methylpyrrolidone is especially preferable from the standpoints that a boiling point thereof is close to that of 1,4BG that is the raw material; and that the stability is high.

The raw material liquid which is used in the present invention may contain only one kind of the above-described amine or may contain two or more kinds thereof. The raw material liquid which is used in the present invention may contain only one kind of the above-described amide or may contain two or more kinds thereof.

In addition, the raw material liquid which is used in the present invention may contain one or two or more kinds of the above-described amine and one or two or more kinds of the above-described amide.

Incidentally, in the case of adding at least one of the amine and the amide in the raw material liquid, at least one of the amine and the amide may be added in the raw material liquid before being introduced into the reactor or may be added in the raw material liquid within the reactor, or it may be added in the both situations.

In the present invention, the water concentration in the raw material liquid is not particularly limited. That is, the effect for reducing BGTF in the presence of at least one of the amine and the amide is achieved in the further presence of water. However, in the present invention, water is formed due to the dehydration cyclization reaction of 1,4BG, and therefore, water may or may not be contained in the raw material liquid at the time of start of the dehydration cyclization reaction.

However, when an excessive large amount of water is contained in the raw material liquid, the volume of the reactor becomes excessive relative to the production capacity of THF, and the dehydration cyclization reaction is further hindered. Therefore, the water concentration is preferably not more than 25% by weight.

In addition, as described above, 1,4BG produced by various known production methods contains a by-product other than BGTF, such as 1-acetoxy-4-hydroxybutane, a dehydrated dimer or dehydrated trimer of 1,4-butanediol, γ-butyrolactone, etc.

Though the content of such a by-product other than BGTF is not particularly limited, it is preferable that the content of such a by-product other than BGTF is small, too. The content of such a by-product other than BGTF and water in the raw material liquid is preferably not more than 0.3% by weight, and especially preferably not more than 0.05% by weight.

In the present invention, the content of BGTF and the content of at least one of the amine and the amide in the raw material liquid to be provided for the reaction may fall within the foregoing ranges. As described above, at least one of the amine and the amide may be added in the raw material liquid before being introduced into the reactor or may be added in the raw material liquid within the reactor, or it may be added in the both situations. However, it is preferable to reduce the content of BGTF in advance by means of the above-described heat treatment or the like and then introduce the raw material liquid having a content of BGTF of from 0.01 to 0.35% by weight, preferably from 0.01 to 0.33% by weight, more preferably from 0.02 to 0.30% by weight, and especially preferably from 0.03 to 0.16% by weight into the reactor.

Incidentally, in the case where the heat treatment is carried out in the presence of at least one of the amine and the amide and in the further presence of water as described, at least one of the amine and the amide is contained in the heat-treated liquid. Therefore, by regulating the amount of at least one of the amine and the amide, which is allowed to exist at the time of heat treatment, to an appropriate amount in the raw material liquid to be provided for the reaction, it is possible to start the dehydration cyclization reaction by introducing the above-described heat-treated liquid directly as the raw material liquid into the reactor.

However, in the case where at least one of the amine and the amide in the heat-treated liquid is short, at least one of the amine and the amide may be added separately.

[Reaction System and Reaction Condition]

In the present invention, the reactor for carrying out the dehydration cyclization reaction is not particularly limited, and a fixed bed reactor filled with a solid catalyst such as a cation exchange resin, etc., a suspended bed reactor using a solid catalyst, or a vessel type or tubular reactor using a homogenous acid catalyst capable of being dissolved in the raw material can be used. In addition, though it may be possible to obtain THF by discharging a solution containing THF and by-product water in a liquid phase part within a reactor from the reactor, followed by purification in post-steps such as a distillation column, etc., it is also possible to extract a part or the whole of THF as a gas containing formed THF and by-product water from a gas phase of the reactor. In that case, the gas extracted from the reactor is condensed by a heat exchanger to obtain a condensed liquid. This heat exchanger is an apparatus for condensing and liquefying a distillate generated from the reactor, and the condensation and liquefaction are carried out by means of heat exchange between an external fluid that is a cooling liquid and a gas.

In addition, by installing a packed column or a plate column in the gas phase part of the reactor, it is possible to distil formed THF and by-product water and also to separate the unreacted raw material to hold it in the liquid phase of the reactor. It is possible to separate the formed THF and by-product water from the unreacted raw material by a distillation column and circulate the unreacted raw material and high-boiling components such as a dimer, etc. into the reactor, or to discharge THF formed through the gas phase and by-product water as a gas from the gas phase part within the reactor, thereby accumulating high-boiling by-products in the liquid phase part within the reactor. Among the high-boiling by-products, it is possible to convert dibutylene glycol that is a dehydrated dimer of 1,4BG, or the like into THF, and by accumulating a part or the whole of these high-boiling by-products in the liquid phase within the reactor, it is possible to reduce the use amount of the raw material, thereby improving the economy. From such reasons, it is preferable to extract a part or the whole of a gas containing THF and water present in the gas phase part within the reactor into the outside of the reactor. In addition, THF and by-product water discharged as the gas may be cooled and condensed, thereby circulating a part thereof as a reflux liquid into the reactor.

In the case of adopting such a reaction mode, namely a mode in which a part or the whole of a gas containing THF and water present in the gas phase part within the reactor is extracted into the outside of the reactor, and the gas is condensed by a heat exchanger, thereby obtaining a mixed liquid containing THF and by-product water as a condensate, a distillation column such as a packed column, a plate column, etc. may be provided in a stage before introducing the above-described gas into the heat exchanger. In that case, though the plate number of the packed column, the plate column, or the like is arbitrary, in general, one plate or more and not more than 100 plates are preferable, and 3 plates or more and not more than 20 plates are especially preferable in terms of theoretical plate. When the plate number is more than the foregoing range, the column becomes excessively large, so that the economy for constructing the facilities is deteriorated. Incidentally, the heat exchanger for liquefaction and condensation of the formed gas described above is provided on the top of the column.

The reaction temperature that is an internal temperature of the liquid phase part within the reactor is in the range of preferably from 80 to 250° C., more preferably from 100 to 200° C., and especially preferably from 120 to 180° C. When the reaction temperature is lower than the foregoing range, the productivity of THF is conspicuously lowered, whereas when it is higher than the foregoing range, a by-product of a minute amount increases, or since the acid catalyst is used, the use of an expensive material as the reactor material becomes essential, and therefore, such is not preferable.

As for the reaction pressure, though an arbitrary pressure can be adopted, it is preferably from 10 to 1,000 kPa, and especially preferably from 100 to 500 kPa in terms of an absolute pressure.

In the present invention, the solution within the reactor mainly contains THF formed by the dehydration cyclization reaction and by-product water, and the like, in addition to the raw material 1,4BG and the acid catalyst. In addition to these materials, the solution within the reactor may also contain a high-boiling compound derived from an impurity in the raw material 1,4BG, a by-product formed from THF and 1,4BG, an acetic acid ester of 1,4BG, or the like.

As described above, the gas containing formed THF and by-product water is discharged from the gas phase part and condensed by the heat exchanger to obtain a condensate, a part of which can be then returned as a reflux liquid into the gas phase part within the reactor. As for a composition of the condensed liquid, though it is possible to contain THF and by-product water in arbitrary concentrations, the THF concentration is in the range of preferably from 30 to 95% by weight, and especially preferably from 50 to 85% by weight. In addition, the present reaction forms by-product water stoichiometrically. For that reason, the water concentration in the condensate is in the range of usually from 1 to 50% by weight, preferably from 5 to 30% by weight, and especially preferably from 15 to 25% by weight.

It is possible to return a part of this condensate as a reflux liquid into the gas phase part within the reactor. On that occasion, a reflux ratio is preferably 0.001 or more and not more than 30, more preferably in the range of from 0.01 to 10, and especially preferably in the range of from 0.1 to 5. Incidentally, in the case where the reflux ratio is too high, the heat source cost for heating increases due to an increase of the required evaporation amount, thereby deteriorating the economy; whereas in the case where the reflux ratio is too low, not only the effect for reducing deposition of a solid is not obtained, but incorporation of a high-boiling component into the distilled condensate due to deterioration of separation thereof is advanced.

A temperature at the time of introducing the formed gas containing THF and by-product water to be introduced into the heat exchanger is in the range of preferably from 10 to 200° C., and especially preferably from 60 to 100° C.

In the present invention, it is also possible to discharge the fluid continuously or intermittently from a series of THF production process (inclusive of not only the reactor but the purification system in the latter stage of the reactor) into the outside of the process. Incidentally, when the fluid is discharged, the fluid may be discharged by once stopping the feed of the raw material 1,4BG to stop the production of THF. The discharged liquid can be subjected to an industrial waste treatment by means of incineration or the like. In addition, the discharged liquid contains the acid catalyst or a solid acid elution fraction such as a cation exchange resin, etc., and therefore, after a neutralization treatment, it is also possible to subject the discharged liquid to an industrial waste treatment by means of incineration or the like.

It is preferable to sufficiently ensure the 1,4BG concentration of the reaction liquid within the reactor during the dehydration cyclization reaction. Specifically, it is preferable to control the 1,4BG concentration of the reaction liquid to from 30 to 99% by weight, preferably from 40 to 90% by weight, and more preferably from 50 to 80% by weight. When the 1,4BG concentration of the reaction liquid is not more than the foregoing upper limit, an abrupt increase of the composition of a polymer that is a high-boiling component can be suppressed and also reduced. When the polymer is excessively accumulated within the reactor, deposition of a solid is advanced in the process, and the operation is hindered due to clogging by staining. On the other hand, what the 1,4BG concentration of the reaction liquid is too low exhibits that a high-boiling fraction such as an unreacted raw material or a dimer, etc. is excessively wasted without being recovered, leading to an increase of the consumption amount of the raw material.

In the present invention, as described above, for the purpose of reducing BGTF derived from the raw material 1,4BG in the presence of at least one of the amine and the amide and by-product water by the dehydration cyclization reaction, thereby effectively controlling the formation of a by-product solid, the amount of at least one of the amine and the amide in the reaction liquid within the reactor during the dehydration cyclization reaction is preferably from 1 to 10,000 ppm by weight in terms of a nitrogen concentration, and the water concentration in this reaction liquid is preferably from 0.1 to 10% by weight.

When the amount of at least one of the amine and the amide of the reaction liquid within the reactor during the dehydration cyclization reaction is smaller than 1 ppm by weight in terms of a nitrogen concentration, the effect for reducing BGTF and the effect for preventing the occurrence of formation of a by-product solid cannot be sufficiently obtained, whereas when it is larger than 10,000 ppm by weight, the productivity of THF is hindered.

Similarly, when the water concentration of the reaction liquid within the reactor during the dehydration cyclization reaction is smaller than 0.1% by weight, the effect for reducing BGTF and the effect for preventing the occurrence of formation of a by-product solid cannot be sufficiently obtained, whereas when it is larger than 10% by weight, the dehydration cyclization reaction is hindered. The water concentration is more preferably from 1% by weight to 6% by weight.

In the present invention, the amount of at least one of the amine and the amide in the reaction liquid within the reactor during the dehydration cyclization reaction is preferably from 1 to 10,000 ppm by weight, preferably from 1 to 4,000 ppm by weight, and more preferably from 11 to 650 ppm by weight in terms of a nitrogen concentration, and the water concentration is preferably from 0.1 to 10% by weight, more preferably from 0.1 to 5% by weight, and still more preferably from 0.1 to 3% by weight.

Incidentally, in the case where the reaction liquid within the reactor during the dehydration cyclization reaction contains only the amine but does not contain the amide, the amount of the amine in the reaction liquid is from 1 to 10,000 ppm by weight, preferably from 8 to 800 ppm by weight, and more preferably from 11 to 650 ppm by weight in terms of a nitrogen concentration.

In addition, in the case where the reaction liquid within the reactor during the dehydration cyclization reaction contains only the amide but does not contain the amine, the amount of the amide in the reaction liquid is from 1 to 10,000 ppm by weight, preferably from 8 to 800 ppm by weight, and more preferably from 20 to 650 ppm by weight in terms of a nitrogen concentration.

In addition, in the case where the reaction liquid within the reactor during the dehydration cyclization reaction contains the amine and the amide, a total amount of the amine and the amide in the reaction liquid is from 1 to 10,000 ppm by weight, preferably from 8 to 800 ppm by weight, and more preferably from 11 to 650 ppm by weight in terms of a nitrogen concentration.

In general, the content of at least one of the amine and the amide in the raw material liquid at the time of start of the dehydration cyclization reaction is from 1 to 1,000 ppm by weight, and it does not fall below the lower limit of the amount of at least one of the amine and the amide in the reaction liquid during the dehydration cyclization reaction. However, in the case where the amount of at least one of the amine and the amide increases during the long-term operation or due to an increase of the concentration of at least one of the amine and the amide, it is preferable to control the amount of at least one of the amine and the amide in the reaction liquid during the dehydration cyclization reaction to not more than the above-described upper limit by discharging the reaction liquid.

In addition, in the case where the water concentration falls outside the above-described preferred range, it is preferable to adjust the concentration by addition of water or distillation of water.

Incidentally, in the present invention, the terms "at the time of start of the dehydration cyclization reaction" refer to a time of introducing the raw material liquid into the reactor and starting heating, and the terms "during the dehydration cyclization reaction" refer to a period during which after this start of heating, the temperature of the reaction liquid within the reactor is kept at a prescribed reaction temperature.

In addition, the reaction liquid within the reactor during the dehydration cyclization reaction refers to a mixed solution of the raw material 1,4BG, the acid catalyst, THF, water, the high-boiling compound derived from an impurity in the raw material 1,4BG, BGTF, at least one of the amine and the amide, the by-product formed from THF and 1,4BG, and the like.

EXAMPLES

The present invention is hereunder described in more detail by reference to the following Examples, but it should not be construed that the present invention is limited to these Examples so long as the gist of the present invention is not deviated.

Incidentally, in the following Examples, the analysis of water was carried out by adopting the Karl Fisher's method.

Each of 1,4-butanediol, tetrahydrofuran, and 2-(4-hydroxybutoxy)-tetrahydrofuran was analyzed by means of gas chromatography and calculated from a peak area ratio of a chromatogram. That is, a value obtained by subtracting a water concentration (% by weight) from 100% by weight, and the weight % value after subtracting the water concentration was multiplied by the area ratio of each of the components of the gas chromatography.

The analysis of nitrogen was carried out by combusting a sample in an argon and oxygen atmosphere and analyzing a generated combustion gas by a trace nitrogen analyzer (TN-10 Model, manufactured by Mitsubishi Chemical Analytech Co., Ltd.) adopting a combustion and reduced pressure chemiluminescence method.

In addition, "DIAION (registered trademark) WA20", manufactured by Mitsubishi Chemical Corporation, that is a weakly basic anion exchange resin having a polyethylenediamine skeleton, was used as an anion exchange resin for making an amine present in 1,4-butanediol. By using this anion exchange resin, it is possible to make a polyamine containing from 2 to 20 constituent units derived from ethyleneamine present in 1,4-butanediol.

Example 1

In a 1,000-mL glass-made flask, 350 g of crude 1,4BG and 35 g of the anion exchange resin were charged, and after stirring at room temperature for 2 hours, the anion exchange resin was separated by means of filtration. As a result of measuring a BGTF concentration in a liquid after adding 70 g of water to 320 g of the obtained filtrate, it was found to be 0.2206% by weight. At that time, this liquid had a water concentration of 24.7% by weight, a 1,4BG concentration of 74.99% by weight, a content of a polyamine eluted from the anion exchange resin of 110 ppm by weight in terms of a concentration as converted into a nitrogen atom, and a pH of 8.6.

A 1,000-mL stainless steel-made autoclave was filled with the present solution, and the inside of the autoclave was substituted with a nitrogen gas, followed by heating at 170° C. for 2 hours. As a result of analyzing the heat-treated liquid, the BGTF concentration was reduced to 0.1522% by weight. Production of THF was carried out by using this heat-treated liquid (water concentration: 24.7% by weight, 1,4BG concentration: 75.0% by weight, nitrogen concentration: 110 ppm, BGTF concentration: 0.1522% by weight) as a raw material liquid.

In a 500-mL glass-made flask reactor equipped with a glass-made cooling tube for distillation, 370.3 g of the heat-treated liquid (1,4BG amount: 277.7 g) was added, 1.51 g of p-toluenesulfonic acid (0.41% by weight relative to the reaction liquid) was charged, and heating was carried out by using an oil bath such that the internal liquid temperature reached 145° C. After the internal liquid temperature became stable at 145° C., a distillate containing THF which had been condensed by the cooling tube was extracted into a glass-made storage vessel.

The amount of the distillate containing THF was 340.2 g. The distillate had a composition of 58.1% by weight of THF and 41.2% by weight of water. A yield of THF was 88.9%, and a formation rate of THF was 51.1 g/hr. Incidentally, the amount of a residue within the flask reactor was 25.4 g, a water concentration was 1.3% by weight, and a nitrogen concentration was 1,603 ppm by weight. The amount of a solid in the residue within the flask reactor was 0.6 mg. A (yield of by-product solid (ppm by weight))/(yield of THF) ratio was 2. The results are summarized and shown in Table 1.

Example 2

In a 1,000-mL glass-made flask, 600 g of crude 1,4BG and 60 g of the anion exchange resin were charged, and after stirring at room temperature for 2 hours, the anion exchange resin was separated by means of filtration. As a result of measuring a BGTF concentration in a liquid after adding 105 g of water to 520 g of the obtained filtrate, it was found to be 0.2206% by weight. At that time, this liquid had a water concentration of 21.0% by weight, a 1,4BG concentration of 78.71% by weight, a content of a polyamine eluted from the anion exchange resin of 110 ppm by weight in terms of a concentration as converted into a nitrogen atom, and a pH of 8.6.

A 1,000-mL stainless steel-made autoclave was filled with the present solution, and the inside of the autoclave was substituted with a nitrogen gas, followed by heating at 170° C. for 2 hours. As a result of analyzing the heat-treated liquid, the BGTF concentration was reduced to 0.1544% by weight.

In a 1,000-mL glass-made flask reactor equipped with a glass-made cooling tube for distillation, 517 g of the heat-treated liquid was charged, and simple distillation was carried out at a pressure of 0.2 kPa and an internal liquid temperature of 102° C. 173.1 g of a distillate was separated as initial distillation, thereby obtaining 316.9 g of a main distillate composed mainly of 1,4BG. On that occasion, the amount of a still residue was 21.9 g. The main distillate had a 1,4BG concentration of 99.4% by weight, a water concentration of 0.310% by weight, a nitrogen concentration of 57 ppm by weight, and a BGTF concentration of 0.1943% by weight. Production of THF was carried out by using this main distillate as a raw material liquid.

In a 500-mL glass-made flask reactor equipped with a glass-made cooling tube for distillation, 300.2 g of the main distillate (1,4BG amount: 298.4 g) was added; 1.50 g of p-toluenesulfonic acid (0.5% by weight relative to the reaction liquid) was charged; reactive distillation was carried out at 145° C. by using an oil bath in the same manner as that in Example 1, thereby extracting 271.0 g of a distillate containing THF into a glass-made storage vessel; and 27.3 g of a residue was obtained within the flask reactor. The amount of a solid in the residue within the flask reactor was 0.2 mg. A (yield of by-product solid (ppm by weight))/(yield of THF) ratio was 1.

The reaction results at that time are summarized and shown in Table 1.

Example 3

In a 1,000-mL glass-made flask, 600 g of crude 1,4BG and 60 g of the anion exchange resin were charged, and after stirring at room temperature for 2 hours, the anion exchange resin was separated by means of filtration. 4.0 g of the obtained filtrate was diluted with 400 g of crude 1,4BG, thereby preparing raw material 1,4BG containing a polyamine eluted from the anion exchange resin in a concentration, as converted into a nitrogen atom, of 1.1 ppm by weight (water concentration: 0.029% by weight, 1,4BG concentration: 99.7% by weight, nitrogen concentration: 1.1 ppm by weight, BGTF concentration: 0.2902% by weight). Incidentally, as a result of measuring a pH, it was found to be 7.0.

In a 500-mL glass-made flask reactor equipped with a glass-made cooling tube for distillation, 300.0 g of the raw material 1,4BG was added; 1.50 g of p-toluenesulfonic acid (0.5% by weight relative to the reaction liquid) was charged; reactive distillation was carried out at 145° C. by using an oil bath in the same manner as that in Example 1, thereby extracting 271.0 g of a distillate containing THF into a glass-made storage vessel; and 28.8 g of a residue was obtained within the flask reactor. The amount of a solid in the residue within the flask reactor was 0.9 mg. A (yield of by-product solid (ppm by weight))/(yield of THF) ratio was 3.

Incidentally, a nitrogen concentration in the raw material liquid within the reactor at the time of start of the dehydration cyclization reaction was 1.1 ppm by weight.

The reaction results at that time are summarized and shown in Table 1.

Example 4

The same procedures as those in Example 3 were carried out, except that 1,4BG having a BGTF concentration of 0.3236% by weight and containing 4-hydroxypiperidine (abbreviated as "4OHP") in a concentration, as converted into a nitrogen atom, of 56.0 ppm by weight was used as the raw material 1,4BG. Incidentally, a nitrogen concentration in the raw material liquid within the reactor at the time of start of the dehydration cyclization reaction was 56.0 ppm by weight. Even in the following Examples and Comparative Examples, the nitrogen concentration in the raw material liquid within the reactor at the time of start of the dehydration cyclization reaction is substantially equal to the concentration, as converted into a nitrogen atom, of the raw material 1,4BG.

265.1 g of a distillate containing THF was extracted into a glass-made storage vessel, thereby obtaining 27.5 g of a residue within the flask reactor. The amount of a solid in the residue within the flask reactor was 0.3 mg. A (yield of by-product solid (ppm by weight))/(yield of THF) ratio was 1.

The reaction results at that time are summarized and shown in Table 1.

Example 5

The reaction was carried out in the same manner as that in Example 3, except that 1,4BG containing 4-hydroxypiperidine (4OHP) in a concentration, as converted into a nitrogen atom, of 10.0 ppm by weight was used as the raw material 1,4BG.

263.0 g of a distillate containing THF was extracted into a glass-made storage vessel, thereby obtaining 36.9 g of a residue within the flask reactor. The amount of a solid in the residue within the flask reactor was 0.8 mg. A (yield of by-product solid (ppm by weight))/(yield of THF) ratio was 3.

The reaction results at that time are summarized and shown in Table 1.

Example 6

The reaction was carried out in the same manner as that in Example 3, except that 1,4BG containing 4-hydroxypiperidine (4OHP) in a concentration, as converted into a nitrogen atom, of 1.1 ppm by weight was used as the raw material 1,4BG.

260.9 g of a distillate containing THF was extracted into a glass-made storage vessel, thereby obtaining 39.2 g of a residue within the flask reactor. The amount of a solid in the residue within the flask reactor was 0.6 mg. A (yield of by-product solid (ppm by weight))/(yield of THF) ratio was 2.

The reaction results at that time are summarized and shown in Table 1.

Example 7

The reaction was carried out in the same manner as that in Example 3, except that 1,4BG containing 1-aminodecane in a concentration, as converted into a nitrogen atom, of 10.0 ppm by weight was used as the raw material 1,4BG in place of the 4-hydroxypiperidine.

274.6 g of a distillate containing THF was extracted into a glass-made storage vessel, thereby obtaining 25.3 g of a residue within the flask reactor. The amount of a solid in the residue within the flask reactor was 1.2 mg. A (yield of by-product solid (ppm by weight))/(yield of THF) ratio was 4.

The reaction results at that time are summarized and shown in Table 1.

Example 8

The reaction was carried out in the same manner as that in Example 3, except that 1,4BG containing tri-n-butylamine in a concentration, as converted into a nitrogen atom, of 10.0 ppm by weight was used as the raw material 1,4BG in place of the 4-hydroxypiperidine.

264.9 g of a distillate containing THF was extracted into a glass-made storage vessel, thereby obtaining 35.1 g of a residue within the flask reactor. The amount of a solid in the residue within the flask reactor was 0.8 mg. A (yield of by-product solid (ppm by weight))/(yield of THF) ratio was 3.

The reaction results at that time are summarized and shown in Table 1.

Example 9

The reaction was carried out in the same manner as that in Example 3, except that 1,4BG containing 2-pyrrolidone (abbreviated as "2P") in a concentration, as converted into a nitrogen atom, of 10.0 ppm by weight was used as the raw material 1,4BG in place of the 4-hydroxypiperidine.

265.8 g of a distillate containing THF was extracted into a glass-made storage vessel, thereby obtaining 34.2 g of a residue within the flask reactor. The amount of a solid in the residue within the flask reactor was 0.9 mg. A (yield of by-product solid (ppm by weight))/(yield of THF) ratio was 3.

The reaction results at that time are summarized and shown in Table 1.

Comparative Example 1

The reaction was carried out in the same manner as that in Example 3, except that 1,4BG having a BGTF concentration of 0.3236% by weight and a nitrogen concentration of not more than 0.1 ppm by weight was used as the raw material 1,4BG.

260.9 g of a distillate containing THF was extracted into a glass-made storage vessel, thereby obtaining 34.7 g of a residue within the flask reactor. The amount of a solid in the residue within the flask reactor was 140 mg. A (yield of by-product solid (ppm by weight))/(yield of THF) ratio was 54.

The reaction results at that time are summarized and shown in Table 2.

Comparative Example 2

The reaction was carried out in the same manner as that in Example 3, except that 1,4BG containing a polyamine eluted from the anion exchange resin in a concentration, as converted into a nitrogen atom, of 0.5 ppm by weight was used as the raw material 1,4BG.

272.1 g of a distillate containing THF was extracted into a glass-made storage vessel, thereby obtaining 27.9 g of a residue within the flask reactor. The amount of a solid in the residue within the flask reactor was 180 mg. A (yield of by-product solid (ppm by weight))/(yield of THF) ratio was 62.

The reaction results at that time are summarized and shown in Table 2.

Comparative Example 3

The reaction was carried out in the same manner as that in Example 3, except that 1,4BG containing 4-hydroxypiperidine (4OHP) in a concentration, as converted into a nitrogen atom, of 0.5 ppm by weight was used as the raw material 1,4BG.

267.6 g of a distillate containing THF was extracted into a glass-made storage vessel, thereby obtaining 32.4 g of a residue within the flask reactor. The amount of a solid in the residue within the flask reactor was 110 mg. A (yield of by-product solid (ppm by weight))/(yield of THF) ratio was 39.

The reaction results at that time are summarized and shown in Table 2.

Comparative Example 4

The reaction was carried out in the same manner as that in Example 3, except that 1,4BG having a 2N—NaOH aqueous solution added thereto such that it was contained in a concentration, as converted into an Na atom, of 100.0 ppm by weight was used as the raw material 1,4BG.

274.0 g of a distillate containing THF was extracted into a glass-made storage vessel, thereby obtaining 26.0 g of a residue within the flask reactor. The amount of a solid in the residue within the flask reactor was 120 mg. A (yield of by-product solid (ppm by weight))/(yield of THF) ratio was 43.

The reaction results at that time are summarized and shown in Table 2.

Comparative Example 5

The reaction was carried out in the same manner as that in Example 3, except that 1,4BG containing a 25% ammonia aqueous solution in a concentration, as converted into a nitrogen atom, of 10.0 ppm by weight was used as the raw material 1,4BG.

268.4 g of a distillate containing THF was extracted into a glass-made storage vessel, thereby obtaining 31.6 g of a residue within the flask reactor. The amount of a solid in the residue within the flask reactor was 210 mg. A (yield of by-product solid (ppm by weight))/(yield of THF) ratio was 76.

The reaction results at that time are summarized and shown in Table 2.

Comparative Example 6

The reaction was carried out in the same manner as that in Example 3, except that 1,4BG containing 2-pyrrolidone in a concentration, as converted into a nitrogen atom, of 2,000 ppm by weight was used as the raw material 1,4BG.

In the present Comparative Example, a distillation rate of THF was 12 g/h (not more than ¼ of the Examples), and the conversion reaction into THF was conspicuously inhibited.

The reaction results at that time are summarized and shown in Table 2.

Comparative Example 7

The reaction was carried out in the same manner as that in Example 3, except that 1,4BG containing 4-hydroxypiperidine in a concentration, as converted into a nitrogen atom, of 15,000 ppm by weight was used as the raw material 1,4BG.

In the present Comparative Example, even when the internal liquid temperature reached 145° C., a distillate was not obtained. Thereafter, heating was carried out such that the internal liquid temperature reached 160° C. However, even when the internal liquid temperature reached 160° C., a distillate was not obtained.

The reaction results at that time are summarized and shown in Table 2.

TABLE 1

| | | Example 1 | Example 2 | Example 3 | Example 4 | Example 5 |
|---|---|---|---|---|---|---|
| Composition of raw material liquid | Water concentration (% by weight) | 24.7 | 0.310 | 0.029 | 0.305 | 0.029 |
| | 1,4BG concentration (% by weight) | 75.0 | 99.4 | 99.7 | 99.7 | 99.7 |
| | Nitrogen concentration (ppm by weight relative to raw material liquid) | 110 | 57 | 1.1 | 56 | 10 |
| | Compound derived from nitrogen | WA20 | WA20 | WA20 | 4OHP | 4OHP |
| | BGTF concentration (% by weight) | 0.1522 | 0.1943 | 0.2902 | 0.3236 | 0.2902 |
| Reaction results | Composition of distillate | THF concentration (% by weight) | 58.1 | 78.8 | 80.4 | 79.4 | 79.9 |
| | | Water concentration (% by weight) | 41.2 | 19.9 | 19.2 | 20.3 | 19.8 |
| | Yield of THF (%) | 88.9 | 89.4 | 91.1 | 88.9 | 87.5 |
| | Formation rate of THF (g/hr) | 51.1 | 74.9 | 70.3 | 69.0 | 71.7 |
| | Distillation rate (%) | 93.1 | 90.9 | 90.4 | 90.8 | 87.7 |
| | Composition of residue within reactor | Nitrogen concentration (ppm by weight) | 1603 | 627 | 11 | 607 | 81 |
| | | Water concentration (% by weight) | 1.3 | 1.7 | 6.2 | 1.5 | 5.5 |
| | Yield of by-product solid (ppm by weight) | 2 | 1 | 3 | 1 | 2 |
| | (Yield of by-product solid)/(yield of THF) ratio | 2 | 1 | 3 | 1 | 3 |

| | | Example 6 | Example 7 | Example 8 | Example 9 |
|---|---|---|---|---|---|
| Composition of raw material liquid | Water concentration (% by weight) | 0.029 | 0.029 | 0.029 | 0.029 |
| | 1,4BG concentration (% by weight) | 99.7 | 99.7 | 99.7 | 99.7 |

TABLE 1-continued

|  |  |  | | | | |
|---|---|---|---|---|---|---|
| | | concentration (ppm by weight relative to raw material liquid) | 1.1 | 10 | 10 | 10 |
| | | Compound derived from nitrogen | 4OHP | 1-Amino decane | Tri-n-butyl-amine | 2P |
| Reaction results | Composition of distillate | BGTF concentration (% by weight) | 0.2902 | 0.2902 | 0.2902 | 0.2902 |
| | | THF concentration (% by weight) | 79.4 | 79.5 | 79.6 | 80.0 |
| | | Water concentration (% by weight) | 19.8 | 20.3 | 19.8 | 19.6 |
| | Yield of THF (%) | | 86.5 | 90.8 | 88.0 | 88.8 |
| | Formation rate of THF (g/hr) | | 75.2 | 51.0 | 58.5 | 61.2 |
| | Distillation rate (%) | | 87.0 | 91.6 | 88.3 | 88.6 |
| | Composition of residue within reactor | Nitrogen concentration (ppm by weight) | 8 | 118 | 85 | 88 |
| | | Water concentration (% by weight) | 5.5 | 6.2 | 5.7 | 5.8 |
| | Yield of by-product solid (ppm by weight) | | 2 | 4 | 2 | 3 |
| | (Yield of by-product solid)/ (yield of THF) ratio | | 2 | 4 | 3 | 3 |

TABLE 2

| | | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|
| Composition of raw material liquid | Water concentration (% by weight) | 0.029 | 0.029 | 0.029 | 0.248 | 0.038 | 0.029 | 0.305 |
| | 1,4BG concentration (% by weight) | 99.7 | 99.7 | 99.7 | 99.6 | 99.7 | 99.3 | 99.7 |
| | Nitrogen concentration (ppm by weight relative to raw material liquid) | Not more than 0.1 | 0.5 | 0.5 | 100 (Na concentration) | 10 | 2000 | 15000 |
| | Compound derived from nitrogen | — | WA20 | 4OHP | 2N—NaOH aqueous solution | 25% $NH_3$ aqueous solution | 2P | 4OHP |
| Reaction results | Composition of distillate | BGTF concentration (% by weight) | 0.3236 | 0.2902 | 0.2902 | 0.2902 | 0.2902 | 0.2902 | 0.3236 |
| | | THF concentration (% by weight) | 78.8 | 79.6 | 80.6 | 79.8 | 78.9 | Conspicuous delay of the reaction Distillation rate: 12 g/h | Reaction impossible |
| | | Water concentration (% by weight) | 19.9 | 19.6 | 19.2 | 19.6 | 19.6 | | |
| | Yield of THF (%) | 86.3 | 90.3 | 90.0 | 90.5 | 88.1 | | |
| | Formation rate of THF (g/hr) | 87.5 | 62.4 | 63.1 | 58.6 | 68.0 | | |
| | Distillation rate (%) | 88.4 | 90.7 | 89.2 | 91.3 | 89.5 | | |
| | Composition of residue within reactor | Nitrogen concentration (ppm by weight) | Not more than 0.1 | 5 | 5 | 1155 (Na concentration) | 1 | | |
| | | Water concentration (% by weight) | 1.7 | 6.0 | 6.4 | 7 | 7.9 | | |
| | Yield of by-product solid (ppm by weight) | 47 | 56 | 35 | 39 | 67 | | |
| | (Yield of by-product solid)/ (yield of THF) ratio | 54 | 62 | 39 | 43 | 76 | | |

From Examples 1 to 9 and Comparative Examples 1 to 5, it is understood that by using the 1,4BG-containing raw material liquid containing a prescribed amount of at least one of the amine and the amide, though the reaction rate is slightly lowered, the selectivity of a by-product solid which hinders the operation can be significantly reduced, and the yield of THF can be improved while keeping the production amount.

In addition, from Comparative Examples 6 and 7, it is understood that when the amount of at least one of the amine and the amide in the 1,4BG-containing raw material liquid is large, the productivity of THF is lowered, and when it is excessively large, the reaction becomes impossible.

While the invention has been described in detail and with reference to specific embodiments thereof, it will be apparent to one skilled in the art that various changes and modifications can be made therein without departing from the spirit and scope thereof. The present application is based on a Japanese patent application filed on Jul. 4, 2011 (Japanese Patent Application No. 2011-148327), a Japanese patent application filed on Jul. 4, 2011 (Japanese Patent Application No. 2011-148328), a Japanese patent application filed on Jul. 8, 2011 (Japanese Patent Application No. 2011-151716), a Japanese patent application filed on Jul. 13, 2011 (Japanese Patent Application No. 2011-154862), a Japanese patent application filed on Aug. 1, 2011 (Japanese Patent Application No. 2011-168645), a Japanese patent application filed on Nov. 1, 2011 (Japanese Patent Application No. 2011-240422), and a Japanese patent application filed on Nov. 2, 2011 (Japanese Patent Application No. 2011-241572), the contents of which are incorporated herein by reference.

The invention claimed is:

1. A method for producing tetrahydrofuran, comprising:
feeding a raw material liquid in a reactor, wherein the raw material liquid comprises 1,4-butanediol, from 0.01 to 0.35% by weight of 2-(4-hydroxybutoxy)-tetrahydrofuran, and 1 ppm by weight or more and not more than 1,000 ppm by weight of at least one of an amine and an amide in terms of a concentration as converted into a nitrogen atom; and
carrying out a dehydration cyclization reaction of 1,4-butanediol in the reactor in the presence of an acid catalyst having a pKa value of not more than 4.

2. A method for producing tetrahydrofuran, comprising:
carrying out a dehydration cyclization reaction of 1,4-butanediol in a reactor in the presence of an acid catalyst having a pKa value of not more than 4,
wherein a reaction liquid within the reactor comprises 1 ppm by weight or more and not more than 10,000 ppm by weight of at least one of an amine and an amide in terms of a concentration as converted into a nitrogen atom.

3. The method according to claim 1,
wherein a reaction liquid within the reactor comprises 1 ppm by weight or more and not more than 10,000 ppm by weight of the at least one of an amine and an amide in terms of a concentration as converted into a nitrogen atom.

4. The method according to claim 1,
wherein a reaction liquid within the reactor comprises 0.1% by weight or more and not more than 10% by weight of water.

5. The method according to claim 1, further comprising:
extracting a gas comprising tetrahydrofuran and water present in a gas phase within the reactor to outside of the reactor.

6. The method according to claim 1,
wherein a temperature of a reaction liquid within the reactor is 80° C. or higher and not higher than 250° C.

7. The method according to claim 1, further comprising:
heating crude 1,4-butanediol at 80° C. or higher in the presence of at least one of an amine and an amide to reduce a content of 2-(4-hydroxybutoxy)-tetrahydrofuran in the crude 1,4-butanediol, prior to the feeding.

8. The method according to claim 2,
wherein the reaction liquid within the reactor comprises 0.1% by weight or more and not more than 10% by weight of water.

9. The method according to claim 2, further comprising:
extracting a gas comprising tetrahydrofuran and water present in a gas phase within the reactor to outside of the reactor.

10. The method according to claim 2,
wherein a temperature of the reaction liquid within the reactor is 80° C. or higher and not higher than 250° C.

11. The method according to claim 2, further comprising:
heating crude 1,4-butanediol at 80° C. or higher in the presence of the at least one of an amine and an amide to reduce a content of 2-(4-hydroxybutoxy)-tetrahydrofuran in the crude 1,4-butanediol, prior to the carrying out of the dehydration cyclization reaction of 1,4-butanediol.

12. The method according to claim 1, wherein the acid catalyst is organic sulfonic acid.

13. The method according to claim 2, wherein the acid catalyst is organic sulfonic acid.

14. The method according to claim 1,
wherein the amine is at least one selected from the group consisting of octylamine, nonylamine, 1-aminodecane, aniline, phenethylamine, dipentylamine, dihexylamine, diheptylamine, dicyclohexylamine, N-methylaniline, tributylamine, tripentylamine, N,N-dimethylaniline, 1,3-propanediamine, N,N-dimethyl-1,6-hexanediamine, N-butylpyrrole, N-butyl-2,3-dihydropyrrole, N-butylpyrrolidine, 2,3-dihydro-1H-indole, 4-aminomethylpiperidine, 4-dimethylaminopyridine, 1,2,3,4-tetrahydroquinoline, 4-amino-5,6-dihydro-2-methylpyrimidine, 2,3,5,6-tetramethylpyrazine, 3,6-dimethylpyridazine, 4-aminobutanol, 2-aminobutanol, 2-ethylmorpholine, N-methoxycarbonylmorpholine, prolinol, 3-hydroxypiperidine, 4-hydroxypiperidine, tetrahydrofurfurylamine, and 3-aminotetrahydropyran, and
the amide is at least one selected from the group consisting of acetamide, N-methylacetamide, N-ethylacetamide, N,N-dimethylacetamide, benzamide, 2-pyrrolidone, N-methylpyrrolidone, N-ethylpyrrolidone, N-vinylpyrrolidone, 2-piperidone, and N-methylpiperidone.

15. The method according to claim 2,
wherein the amine is at least one selected from the group consisting of octylamine, nonylamine, 1-aminodecane, aniline, phenethylamine, dipentylamine, dihexylamine, diheptylamine, dicyclohexylamine, N-methylaniline, tributylamine, tripentylamine, N,N-dimethylaniline, 1,3-propanediamine, N,N-dimethyl-1,6-hexanediamine, N-butylpyrrole, N-butyl-2,3-dihydropyrrole, N-butylpyrrolidine, 2,3-dihydro-1H-indole, 4-aminomethylpiperidine, 4-dimethylaminopyridine, 1,2,3,4-tetrahydroquinoline, 4-amino-5,6-dihydro-2-methylpyrimidine, 2,3,5,6-tetramethylpyrazine, 3,6-dimethylpyridazine, 4-aminobutanol, 2-aminobutanol, 2-ethylmorpholine, N-methoxycarbonylmorpholine, prolinol, 3-hydroxypiperidine, 4-hydroxypiperidine, tetrahydrofurfurylamine, and 3-aminotetrahydropyran, and
the amide is at least one selected from the group consisting of acetamide, N-methylacetamide, N-ethylacetamide, N,N-dimethylacetamide, benzamide, 2-pyrrolidone, N-methylpyrrolidone, N-ethylpyrrolidone, N-vinylpyrrolidone, 2-piperidone, and N-methylpiperidone.

16. The method according to claim 7, wherein the heating of the crude 1,4-butanediol is carried out such that the raw material liquid comprises from 0.01 to 0.35% by weight of 2-(4-hydroxybutoxy)-tetrahydrofuran.

17. The method according to claim 7, wherein the crude 1,4-butanediol has a pH value of from 7 to 12.

18. The method according to claim 1, wherein the acid catalyst is a metal-free organic acid or a metal-free phosphoric acid.

19. The method according to claim 2, wherein the acid catalyst is a metal-free organic acid or a metal-free phosphoric acid.

* * * * *